(12) United States Patent
Tkebuchava

(10) Patent No.: US 9,011,380 B2
(45) Date of Patent: Apr. 21, 2015

(54) CATHETER FOR INTRODUCTION OF MEDICATIONS TO THE TISSUES OF A HEART OR OTHER ORGAN

(76) Inventor: Tengiz Tkebuchava, Newton, MA (US)

( * ) Notice: Subject to any disclaimer, the term of this patent is extended or adjusted under 35 U.S.C. 154(b) by 932 days.

(21) Appl. No.: 12/722,931

(22) Filed: Mar. 12, 2010

(65) Prior Publication Data

US 2010/0168713 A1    Jul. 1, 2010

Related U.S. Application Data

(62) Division of application No. 11/152,398, filed on Jun. 14, 2005, now Pat. No. 7,691,086.

(51) Int. Cl.
*A61M 25/00* (2006.01)
*A61B 5/00* (2006.01)
(Continued)

(52) U.S. Cl.
CPC ............ *A61M 25/003* (2013.01); *A61B 5/4839* (2013.01); *A61B 2017/00247* (2013.01); *A61B 2018/00392* (2013.01); *A61M 25/0071* (2013.01); *A61M 25/0084* (2013.01); *A61M 2025/0002* (2013.01);
(Continued)

(58) Field of Classification Search
USPC .......... 604/164.01, 164.07, 272, 158, 166.01, 604/164.04, 95.01, 95.04; 606/186, 198
See application file for complete search history.

(56) References Cited

U.S. PATENT DOCUMENTS

| | | |
|---|---|---|
| 4,759,378 A | 7/1988 | Swendson et al. |
| 5,334,168 A | 8/1994 | Hemmer |
| 5,419,777 A | 5/1995 | Hofling |

(Continued)

FOREIGN PATENT DOCUMENTS

| | | |
|---|---|---|
| WO | WO9526776 A1 | 10/1995 |
| WO | WO 9939624 | 8/1999 |

(Continued)

OTHER PUBLICATIONS

Sherman, "Cellular Therapy for Chronic Myocardial Disease: Non-surgical Approaches", "Basic Appl Myol", 2003, pp. 11-14, vol. 13, No. 1, Publisher: The Cardiovascular Institute, Mount Sinai School of Medicine, New York, NY.

*Primary Examiner* — Nathan R Price
(74) *Attorney, Agent, or Firm* — Loginov & Associates, PLLC; William A. Loginov

(57) ABSTRACT

A positionable, direct-injection catheter that can access a specific region of the heart or other organ. The catheter is provided with one or two needle shafts, which may be located within respective sheaths that extend axially along the interior of the lumen of a main catheter shaft. Each needle shaft carries, at a distal end thereof a penetrable element or "needle" that is normally retracted within the distal tip of the main shaft during travel to the target organ, but is subsequently deployed by action of a handle-mounted trigger mechanism to extend the needles into the organ's wall. Each extended needle is curved to relative to the shaft's axis to enter the organ wall in a flattened trajectory that both reduces the chance of puncture through the wall and anchors the needles into the wall during injection (for reduced chance of pullout under pressure). A plurality of apertures which provide for more complete agent delivery rapidly, while maintaining a low delivery velocity to effect treatment delivery in as short a period of time as possible without the problems caused by high velocity delivery. The needles are typically arranged to exit the tip at contralateral orientations relative to each other.

22 Claims, 6 Drawing Sheets

(51) Int. Cl.
*A61B 17/00* (2006.01)
*A61B 18/00* (2006.01)

(52) U.S. Cl.
CPC ............... *A61M 2025/0037* (2013.01); *A61M 2025/0086* (2013.01); *A61M 2025/0096* (2013.01)

(56) References Cited

U.S. PATENT DOCUMENTS

| | | | |
|---|---|---|---|
| 5,464,395 | A | 11/1995 | Faxon et al. |
| 5,921,982 | A | 7/1999 | Lesh et al. |
| 6,217,554 | B1 | 4/2001 | Green |
| 6,254,573 | B1 | 7/2001 | Haim et al. |
| 6,293,958 | B1 | 9/2001 | Berry et al. |
| 6,302,875 | B1 | 10/2001 | Makower et al. |
| 6,322,536 | B1 | 11/2001 | Rosengart et al. |
| 6,346,095 | B1 | 2/2002 | Gross et al. |
| 6,432,092 | B2 | 8/2002 | Miller |
| 6,605,061 | B2 | 8/2003 | VanTassel et al. |
| 6,692,466 | B1 | 2/2004 | Chow et al. |
| 6,716,196 | B2 | 4/2004 | Lesh et al. |
| 6,726,662 | B2 | 4/2004 | Altman |
| 6,730,061 | B1 | 5/2004 | Cuschieri et al. |
| 6,770,066 | B1 | 8/2004 | Weaver et al. |
| 6,829,497 | B2 | 12/2004 | Mogul |
| 2001/0007933 | A1* | 7/2001 | Lesh et al. ............ 604/272 |
| 2002/0016622 | A1* | 2/2002 | Janke et al. ............ 607/116 |
| 2002/0095124 | A1 | 7/2002 | Palasis et al. |
| 2002/0120238 | A1 | 8/2002 | McGuckin, Jr. et al. |
| 2003/0171723 | A1 | 9/2003 | Ponzi |
| 2004/0015061 | A1 | 1/2004 | Currier et al. |
| 2004/0024371 | A1 | 2/2004 | Plicchi et al. |
| 2004/0143197 | A1* | 7/2004 | Soukup et al. ............ 600/585 |
| 2004/0193239 | A1* | 9/2004 | Falwell et al. ............ 607/122 |
| 2005/0133719 | A1 | 6/2005 | Todokoro et al. |
| 2005/0177223 | A1 | 8/2005 | Palmaz |
| 2006/0167418 | A1 | 7/2006 | Khayal et al. |

FOREIGN PATENT DOCUMENTS

| | | |
|---|---|---|
| WO | WO 03006089 A1 | 1/2003 |
| WO | WO 2004030740 A1 | 4/2004 |
| WO | WO 2005025652 A1 | 3/2005 |

* cited by examiner

CATHETER FOR INTRODUCTION OF MEDICATIONS TO THE TISSUES OF A HEART OR OTHER ORGAN

RELATED APPLICATIONS

This application is a divisional of U.S. application Ser. No. 11/152,398, filed Jun. 14, 2005, entitled CATHETER FOR INTRODUCTION OF MEDICATIONS TO THE TISSUES OF A HEART OR OTHER ORGAN, the entire disclosure of which is herein incorporated by reference.

FIELD OF THE INVENTION

The present invention relates generally to catheters designed to deliver therapeutic and/or diagnostic agents to specific areas of the body and, more particularly, to positionable, direct-injection catheters that can access a specific region of the heart via veins or arteries of the body.

BACKGROUND OF THE INVENTION

Diseases of the heart are the major cause of non-accidental death in people over the age of 65 and are the second most common cause for people aged 45-64. A common form of heart disease is ischemic heart disease, which is caused by blockage, or partial blockage, of blood vessels leading to the heart resulting in slow deterioration and eventual death of heart cells. Although there are several treatments available for ischemic heart disease including angioplasty and bypass surgery, these treatments are unavailable for many patients and, for others, they offer only temporary relief.

One promising treatment is the introduction, via a catheter, of specific medicants directly to the heart and/or related blood vessels, such as angiogenesis-promoting substances or gene therapeutic agents. Catheter delivery has the potential to deliver the therapeutic agent or agents by physically placing them exactly where they are needed. Typically, catheters are introduced into the body via the femoral artery and then directed to the heart or other areas. Catheter delivery requires that the catheter be both flexible so as to bend where necessary to follow the blood vessels or arteries and sufficiently rigid so as to be controllable for accurate targeted agent delivery. What is still needed, however, is a catheter that is both flexible and controllable.

Another form of heart disease is abnormal heart rhythms (cardiac arrhythmias). There are a variety of causes of arrhythmias; for example, cardiac valve disease, ischemic heart disease, and rheumatic heart disease may all cause arrhythmias. The contraction of the heart is governed by electrical signals which originate in the right atrium and then are transmitted throughout the heart creating a coordinated heartbeat. Problems arise when other parts of the heart generate electrical signals which are out of phase with the normal signals or when the transmission of the correct signals is perturbed by defects in the conduction system. These difficulties can be overcome by the selective destruction of abnormal cells that are the origin of the electrical problems. This can be accomplished by chemical agent ablation with appropriate chemical agents delivered to the critical part or parts of the heart by means of a suitable catheter. What is still lacking, however, is a mechanism to administer ablating chemical agents accurately to specific areas of the heart using a catheter.

While catheters are a remarkably efficient devices for delivering various kinds of drugs to the heart and associated blood vessels, there still are disadvantages associated with their use that either restrict the use of catheters to patients whose bodies can accept such treatment, or conversely, increase the risk of an adverse outcome for the patient. For example, the passage of the catheter through veins or arteries, especially through femoral arteries, can result in abrasions particularly at locations where the veins or arteries bend sharply on their way to the main coronary blood vessels. Further, once the catheter is inserted, the distal end of the catheter must be positioned exactly for accurate delivery of medication or other treatments via an extendible needle that is retracted during travel of the catheter to the final destination. There is a risk, in that once extended, the needle may scratch or perforate tissue by inadvertent or incorrect movement of the catheter tip. This is particularly problematic in applying an extendible needle to the right ventricle's wall, as it is quite thin and easily punctured. Any over-penetration or abrasion by the extendible needle or underlying catheter can cause bleeding and the formation of blood clots, which are potentially dangerous to the patient. To reduce the potential for clotting, the patient is frequently administered an anticoagulant such as heparin. While this precaution may reduce the chances of accidental blood clotting, it also creates a potential for uncontrolled bleeding internally, which is an equally dangerous situation to be avoided. What would be of great value to both patients and physicians is a device to deliver therapeutic or diagnostic agents, directly to a specific area within the heart, without the need for a blood thinner.

Targeted delivery of a gene therapy agent in a restricted region of the body can be used to modify cells in a desired region of the body. This technique, known as somatic gene therapy, is able to genetically express a therapeutically or diagnostically useful protein. Gene therapy can be a direct in vivo process in which genetic material is transferred to cells in the desired region of the patient's body. Alternatively, cells from the targeted region can be harvested, genetic material transferred to the cells, and the modified cells thereafter implanted back into the patient's body.

When using the direct in vivo method, a major concern is to avoid inserting the agent into a rapidly dividing cell population. This situation would substantially reduce the duration of the desired DNA transgene expression when using certain viral vectors such as the common adenovirus vectors. It is important, therefore, that the desired transgene or desired DNA is targeted so that, (1) only the desired cells will receive and express the gene, and (2) the gene will not be systemically distributed.

Currently, gene therapy for the heart muscle is still in the development stage. There have been studies of experimental gene therapy in rats by direct injection of DNA into the myocardium. The direct injection has caused inflammation, apparent myocyte necrosis, and scar tissue-formation along the needle tracks. Gene transfer using adenovirus vectors injected into pig hearts has been shown to be highly efficient in regions immediately adjacent to the injection, but evidence of gene transfer occurred only in a small region of the myocardium. A prominent inflammatory response has been associated with these injections, in part because current procedures utilizing catheters require that the catheter be inserted at the femoral artery. In order to overcome these difficulties, it is desirable to have the mechanism to insert a catheter into a body using an artery in an arm, such as a brachial artery or a radial artery. Catheter entry via an artery in the arm allows the patient the ability to walk immediately after an operation simply by keeping the pierced portion of the upper arm in an appropriately outstretched or elevated orientation. Moreover, injection through a brachial or radial artery eliminates potential abdominal-region pain. In order for a catheter to be administered through the brachial or radial artery, the catheter would have to be designed to accommodate the specific needs of subclavian insertion.

Direct injection catheters also may be used in treating disease of other parts of the body. They may be used for the treatment of peripheral vascular disease, which is due to insufficient blood flow to the legs. This procedure delivers recombinant adenovirus expressing an angiogenic peptide or protein to cells of the skeletal muscles via a catheter.

Thus, in spite of the interest in catheter-based treatments, there clearly still remain a number of important difficulties in effectively using this technique. The need for accurate positioning of the distal end of the catheter for delivery of the treatment medium is clear, but this is related to the ability to direct the distal end. Current catheter technology allows the bending of the near distal end in one direction only, thereby limiting the positionability of the tip. Another difficulty is in maintaining the distal end in contact with the tissue to receive treatment for the duration of the delivery activity. Too frequently, once positioned, the distal end moves, and in so doing, scratches or perforates the tissue to be treated thereby promoting bleeding. It is desirable also to effect the treatment delivery in as short a period of time as possible. Another limitation is the volume of liquid that can be passed through the lumen(s) at the distal end of the catheter. Simply pumping liquid at a higher pressure causes other problems because of the recoil of the catheter and hence movement away from the delivery site. It is, thus, highly desirable to provide a catheter capable of accurate positioning, one that allows the distal end to be anchored firmly against the tissue being treated, which can deliver the required quantity of one or more than one treatment agent rapidly but at low velocity, with minimal systemic loss, maintaining the agent in contact with the target tissue for the time required for treatment, which can be operated by a technician with minimal training, and requiring no special assisting technology. Such a catheter should eliminate the possibility of myocardial perforation and valve damage, even when applied to relatively thin wall thicknesses, such as the right ventricular wall.

SUMMARY OF THE INVENTION

This invention overcomes the disadvantages of the prior art by providing a positionable, direct-injection catheters that can access a specific region of the heart or other organ (including the difficult to reach endocardial surfaces) via veins or arteries of the body, including through an artery or vein in the arm, such as a brachial or radial artery or subclavian vein, to provide targeted delivery and release of therapeutic or diagnostic agents, including gene therapy agents over discrete periods of time in a controlled manner minimizing accidental abrasion or perforation of bodily organs. In particular the catheter of the present invention enables access to (via the subclavian vein) and treatment of the thin myocardium of the right ventricle of the heart. Subclavian insertion also means that the catheter length is substantially reduced, which provides for the catheter to be precisely controlled for accurate delivery while offering the degree of flexibility required for the catheter to bend where necessary to follow the blood vessels or arteries.

The catheter of the present invention is provided with one or two needle shafts, which may be located within respective sheaths that extend axially along the interior of the lumen of a main catheter shaft. This main shaft is bendable in one or two orthogonal planes to provide steering. Each needle shaft carries, at a distal end thereof a penetrable element or "needle" that is normally retracted within the distal tip of the main shaft during travel to the target organ, but is subsequently deployed by action of a handle-mounted trigger mechanism to extend the needles into the organ's wall. Each extended needle is curved (by means of memory metal-construction) to an angle of approximately 70-80 degrees relative to the shaft's axis of extension, to enter the organ wall in a flattened trajectory that both reduces the chance of puncture through the wall and anchors the needles into the wall during injection (for reduced chance of pullout under pressure). To deliver desired therapeutic and/or diagnostic agents each needle is provided with a plurality of apertures which provide for more complete agent delivery rapidly, while maintaining a low delivery velocity to effect treatment delivery in as short a period of time as possible without the problems caused by high velocity delivery. Typically apertures are provided along the medial side of each needle as well as the tip. The main shaft's lumen can also carry an agent, such as a dye or a guided smaller tube or catheter having, for example a sensor or probe. The shaft tip may include an integral probe for blood pressure, and the like. Each needle can include an internal sensor, such as a DNA sensor. Signals can be transmitted down the shaft to the handle, and whence to a monitor using a variety of techniques.

In an illustrative embodiment, the needles are arranged to that when they are extended from the distal tip of the catheter shaft they curve away from each other in a contralateral fashion at the selected angle and, thereby attach themselves to the targeted tissue and anchor the catheter in place for the duration of treatment.

BRIEF DESCRIPTION OF THE DRAWINGS

The invention description below refers to the accompanying drawings, of which.

DETAILED DESCRIPTION

Definitions

The following general definitions are provided for terms of common usage herein, but such terms should be taken broadly to include a variety of equivalent structures and or functional elements where appropriate:

Catheter, as used herein, refers to a tubular medical device for insertion into canals, vessels, passageways, or body cavities usually to permit injection or withdrawal of fluids or to keep a passage open.

Lumen, as used herein, refers to the bore of a tube, as of a hollow needle or catheter; also as used herein, may refer to the cavity or passageway of a tubular organ, such as a blood vessel.

Memory metal, as used herein, refers to a highly elastic metal that has the tendency to hold its chosen shape despite significant application of deformation thereto. A common type of memory metal is commercially known as "NiTi-NOL", which is used in a vast variety of applications in medical implants and a variety of medical instruments, such as a martensitic instrument used in open heart surgery to measure the inner diameter of the coronary vessels. The use of shape-memory metal element for a particular purpose generally requires the setting of a custom shape in a wire, ribbon, strip, sheet, tubing, or bar. Shape setting is typically accomplished by constraining the memory metal element on a mandrel or fixture of the desired shape and applying an appropriate heat treatment. The heat treatment parameters chosen to set both the shape and the properties of the part are critical, and usually need to be determined experimentally for each desired part's requirements. In general, temperatures as low as 400 deg. C. and times as short as 1-2 minutes can set the shape, but generally one uses a temperature closer to 500 deg. C. and times over 5 minutes. Rapid cooling of some form is preferred via a water quench or rapid air cool (if both the parts and the fixture are small). Higher heat treatment times and temperatures will increase the actuation temperature of the part and often gives a sharper thermal response.

Shaft, as used herein, refers to a hollow elongated cylinder, such as a tube.

It should also be understood that the drawings are not necessarily to scale. In certain instances, details which are not necessary for an understanding of the present invention or which render other details difficult to perceive may have been omitted.

Catheter Insertion and Use

Figure 1:
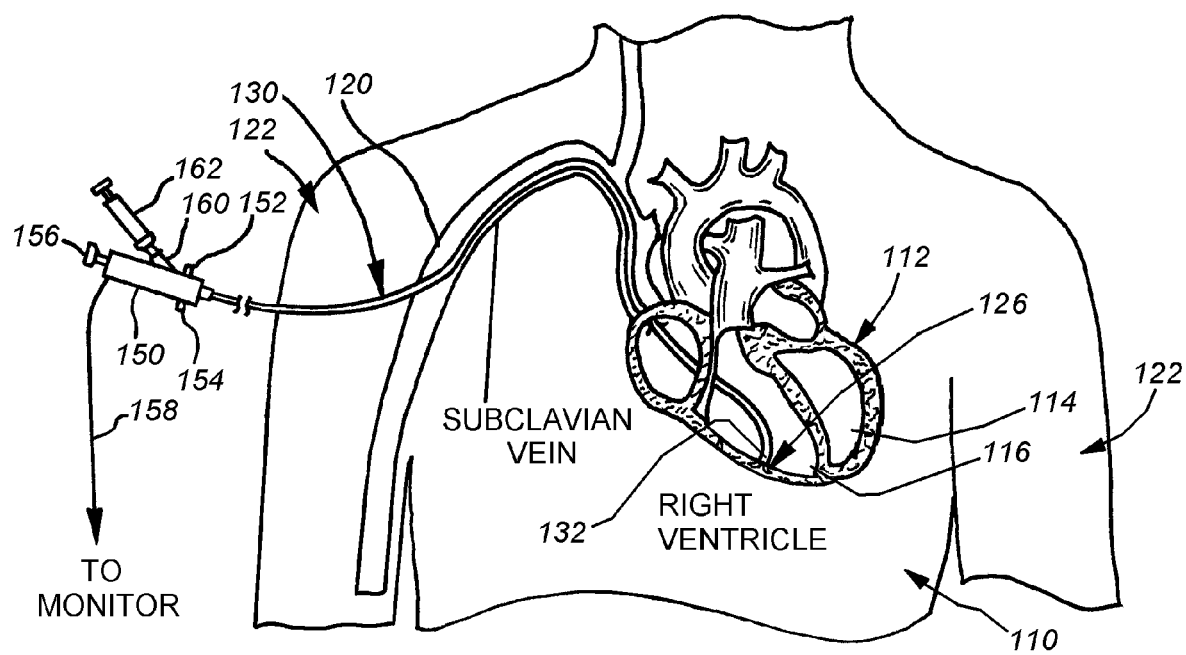
FIG. 1 is is a frontal view of a human torso showing the heart and a pathway, via the subclavian vein, which can be used to pass the catheter of this invention to the right ventricle of the heart.

FIG. 1 is a frontal view of an exemplary human torso 110 showing a portion of the circulatory system including the heart 112 with its left ventricle 114 and right ventricle 116. The right ventricle 116 feeds the subclavian vein 120, which that offers a pathway to pass an injection catheter 130 according to an embodiment of this invention into the right ventricle 116. As will be described in detail below, the distal end 132 of the catheter is provide with a pair of extensible needles that engage and anchor into the desired site (such as the myocardium 126) within the right ventricle 116 to dispense one or more medications (therapeutic or diagnostic agents) in a fluid stream that passes through associated needle lumens. Introducing the direct injection catheter 130 through the subclavian vein 120 in the arm 122, or alternatively through the brachial vein, into the right ventricle 116 provides for the length of the catheter to be substantially reduced, which in turn provides for easier and more accurate positioning of the distal end of the catheter. As also discussed in more detail below, the distal tip of the catheter is positioned by a one-point or two-point bending of the catheter shaft. Where two-point bending is provided, one bending point is close to the distal tip (for example, about 10 cm from the distal tip) and the other bending point being even closer to the distal tip (for example, from about 3 to 5 cm from the distal tip). Having a shorter catheter (for example, the length of the catheter body is from about 50 to 70 cm) shaft provides for greater control of the bending of the two bending points of the shaft. Additionally, being able to insert the catheter through the subclavian vein in the arm or through the brachial vein into a right ventricle is highly significant to the heart diseased patients in whom the atherosclerotic process is occurring throughout the body, the fermoral arteries are atheroscroticaly damaged or totally occluded (closed), or the aorta may be damaged or occluded. In such cases, it is very dangerous, or impossible, to enter via femoral arteries. Using the catheter of the present invention, with its programmed needles (see below) and the thin diameter (for example, having a diameter of from about 3.0 to 1.5 mm throughout its entire length) of its shaft, however, allows catheter entrance through arteries of the arms, which are less vulnerable to the atherosclerotic changes that are occurring throughout the patient's body. Moreover, the catheter can be introduced into the right ventricle from the subclavian vein 120 without using heparin (a blood thinner) and without passing through regions which might be occluded in elderly patients, such as the femoral artery, iliac artery, or the distal aorta.

As described below, the catheter is manipulated, and the catheter's distal end 132 is provided with agents using a positioning handle 150 that can be conventional, or uniquely designed for the requirements of the catheter 130. Briefly, the handle includes a plurality of triggers or controls 152, 154 that operate extension of the needles and steering of the distal end at one or two points. The handle 150 may also contain a hub 156 for connecting a fluid source (dye markers, etc.), electrical connections or (in an alternate embodiment) guiding-in smaller-diameter catheter (not shown). The hub can lead to a central, enlarged lumen within the catheter 130 described further below. A guided-in, smaller-diameter catheter or tube can contain a distal sensor tip or probe that measures one or more predetermined characteristics or vital signs (for example, intracardial blood pressure, pH, DNA, etc.) in an illustrative embodiment. In one embodiment, the tube is connected to a monitor. The pressure is displayed on the monitor by moving waves and digital numbers. Thus, it gives information about the position of the needle: whether it is located in the heart cavity or inserted into the wall. This detector is able to indicate when the needles is not inserted properly into the organ wall or have jumped out of the organ wall during an injection or have spontaneously moved. Thus, these features allow prompt correction of the position of the needle and therefore wasting of a drug is avoided. The detected information is electronically transferred into any ordinary monitor in the hospital room.

Likewise the handle can contain other wired or wireless connections 158 to appropriate monitors (see below) that are operatively connected to sensors that reside variously at or near the distal end 132. Significantly, the handle contains one or more ports 160 in fluid communication with the extensible needles at the distal end 132. Such port(s) receive the delivery end of an appropriate syringe 162 or other fluid-injection mechanism (a powered and/or timed injector, for example). The handle 150 is discussed in further detail below.

Figure 2:
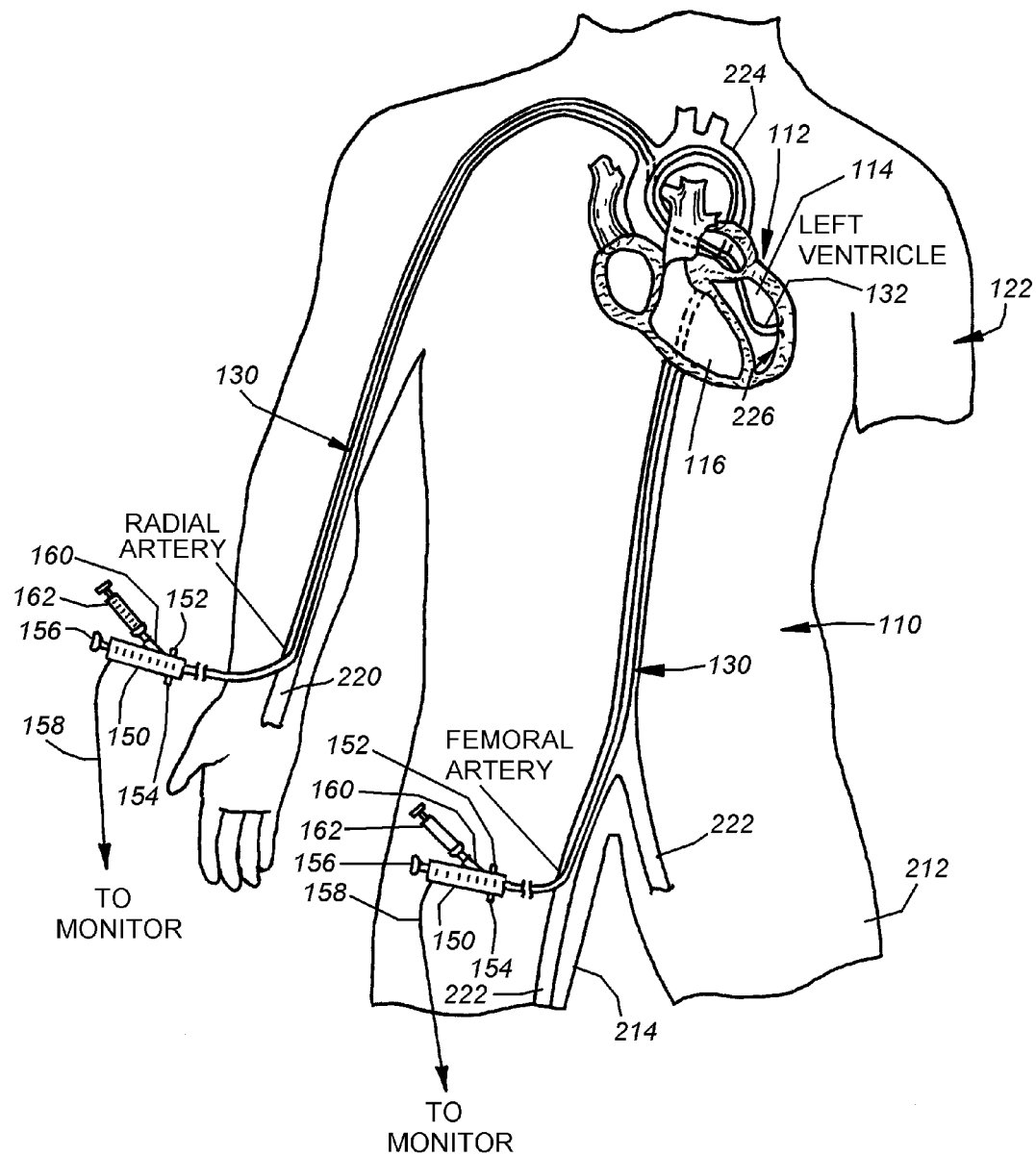
FIG. 2 is a frontal view of a human torso showing the heart and a pathway, via either the radial artery or femoral artery, which can be used to pass a catheter of this invention to the left ventricle of the heart.

Reference is now made to FIG. 2, which shows the extended torso 110 with associated arteries in the arm 122 and legs 212 and 214. By directing the catheter either through the radial artery 220 or the femoral artery 222, treatment of particular sites in the left ventricle 114 can also be accomplished using the catheter 130 of this invention. In this example, the catheter 130 extends from either of alternate paths through the aortic arch 224 and into the left ventricle 114. Within the left ventricle, the distal end 132 engages the myocardium 226 to deliver needed agents as described further below.

Figure 3:
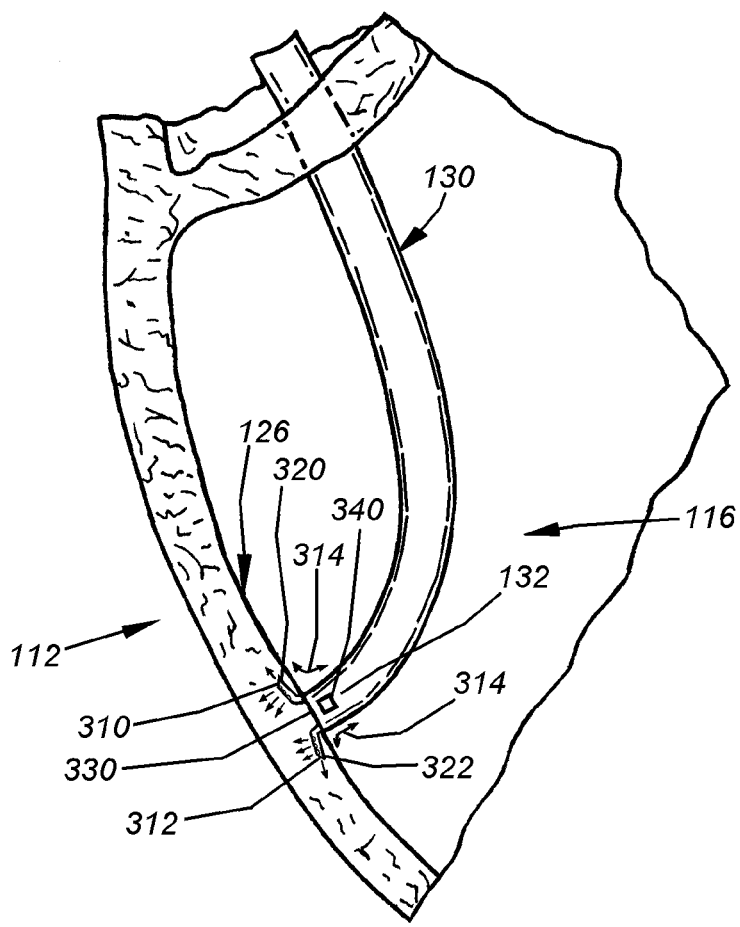
FIG. 3 is a more-detailed partial cross section of the right ventricle of the heart of FIG. 1 showing an exemplary insertion of the extensible needles of the catheter of this invention into the heart wall.

Referring now to FIG. 3, the distal end 132 of the catheter 130 is shown engaging an exemplary site within the right ventricle of the heart 112 in greater detail. In this example, the extensible needles 310 and 312 have been deployed (arrows 314) into the myocardium 126. As will be described below, the memory metal from which the deployable tips of the needles 310, 312 are constructed allows them to store a significantly curvilinear/bent shape that, when extended from the tip 330 of the distal end 132 exhibits a nearly perpendicular (with respect to the tip's axis) direction of extension, in each of opposing directions of extension (i.e., contralateral directions of extension). Once extended, each needle 310 and 312 can deliver a therapeutic and/or diagnostic agent via a tip opening 320, 322, respectively and one or more openings along (at least) the medial edge of the needle's exposed shaft. This provides significant distribution area of an agent, further ensuring that is fills the affected area of the heart and does not overdose a single spot. While not indicated, the center of the tip 330 is hollow, allowing another agent of device to exit therefrom, as described above.

That is, since each needle 310, 312 may be provided with several tiny orifices or apertures, preferably on the medial sides of the needles and at the tips 320, 322, clogging of each needle lumen is reduced, and a desired agent may be delivered more quickly, avoiding the necessity of using high injection pressure in the injection area, which spares cells of the targeted tissue from being damaged. Additionally, the agent dispersed via the multiple apertures more completely infiltrates tissue preventing back leakage from the entry point of the needle, thus, reducing, or eliminating, systemic loss. This is an important point since some physicians perform 20 transendocardial injections placed 1 cm apart between the viable (healthy) and infarcted areas. This means that more volume of injectate is delivered to targeted tissue per injection. Note that a single injection of a therapeutic agent from a catheter of the present invention infiltrates more tissue target area than is possible using existing catheters, which means that multiple endocardial penetrations are avoided, or eliminated. Injections via the needles of existing catheters lead to "islands" of cells in the myocardium, providing a substrate for electrical instability and ventricular tachyarrhythmias. Moreover, studies have shown that reduced injectate volume from 100 to 10 microliters improved microsphere retention, and a trend toward improved viral transfection associated with smaller injection volumes. It is to be expected that a dispersed distribution of the injectate in the tissue (not sack-like accumulation) by the catheter of the present invention should enhance the therapeutic result.

It should also be clear that the multiple needles 310, 312 provided in this embodiment allow for the simultaneous delivery of multiple therapeutic agents (drugs), diagnostic agents, or a combination of drugs and diagnostic agents. The catheter 130, according to an illustrative embodiment, also provides for determining the location of any therapeutic agent in a target tissue, since it allows simultaneous injection both of a drug and a marker (for example, Evan's blue) or two different drugs. The advantage of this consists in delivering two therapeutic agents, e.g. a gene and cells (endothelial progenitor or stem cells, or any other gene/cell combination) which will not only express a synergistic effect but might also show good results using reduced doses of the drugs.

As will be discussed below, accurate placement of the needles 310, 312 into desired tissue is further made possible by the ability to bend the catheter using the positioning handle 150 located at the proximal part of the catheter's tubular shaft. The handle 150 accurately positions the needles 310, 312 by positioning the catheter's distal tip 330 where the needles are to be located. This provides for highly accurate, repeatable agent delivery directly into a specific tissue site. Furthermore, the needle(s) may be repositioned to a different wall of the organ for agent delivery to multiple tissue sites. Where the ability to bend the distal end of the tubular catheter shaft in at least two distinct bending sites is provided, positioning and repositioning of the needle(s) in an arc of approximately 180 degrees is achieved. This positioning of the needle by shaft bending eliminates the need to rotate the needle 180° to reposition it and therefore the bending mechanism reduces the risk of unintentional scraping or puncturing of the myocardial tissue with the tip of the device or needles.

Note that the addition of a special radio-opaque marker 340 (for example) on the distal tip 330 of the catheter 130, as desired, allows one to determine the position of the catheter tip easily on an X-ray screen. Moreover, this ability facilitates the definition of the rotation and angle of the position of the distal end of the catheter of the present invention. This design also allows the determination of whether the needles 310, 312 are extended or retracted.

Also, the ability of the catheter of the present invention to provide an accurate, rapid, and reliable cell transplantation into the septum or near-conducting-system-area will allow the replacement of existing pacing therapies or the treatment of specific arrhythmias. The ability to approach such areas for cell transplantation, as provided by the catheter of the present invention, also complements pacemakers or other devices in the treatment of heart failure by supplementing the sinoatrial or atrial-venticular nodes or improving refractoriness in conditions such as long-QT syndrome.

Catheter Structure and Function

Figure 4:
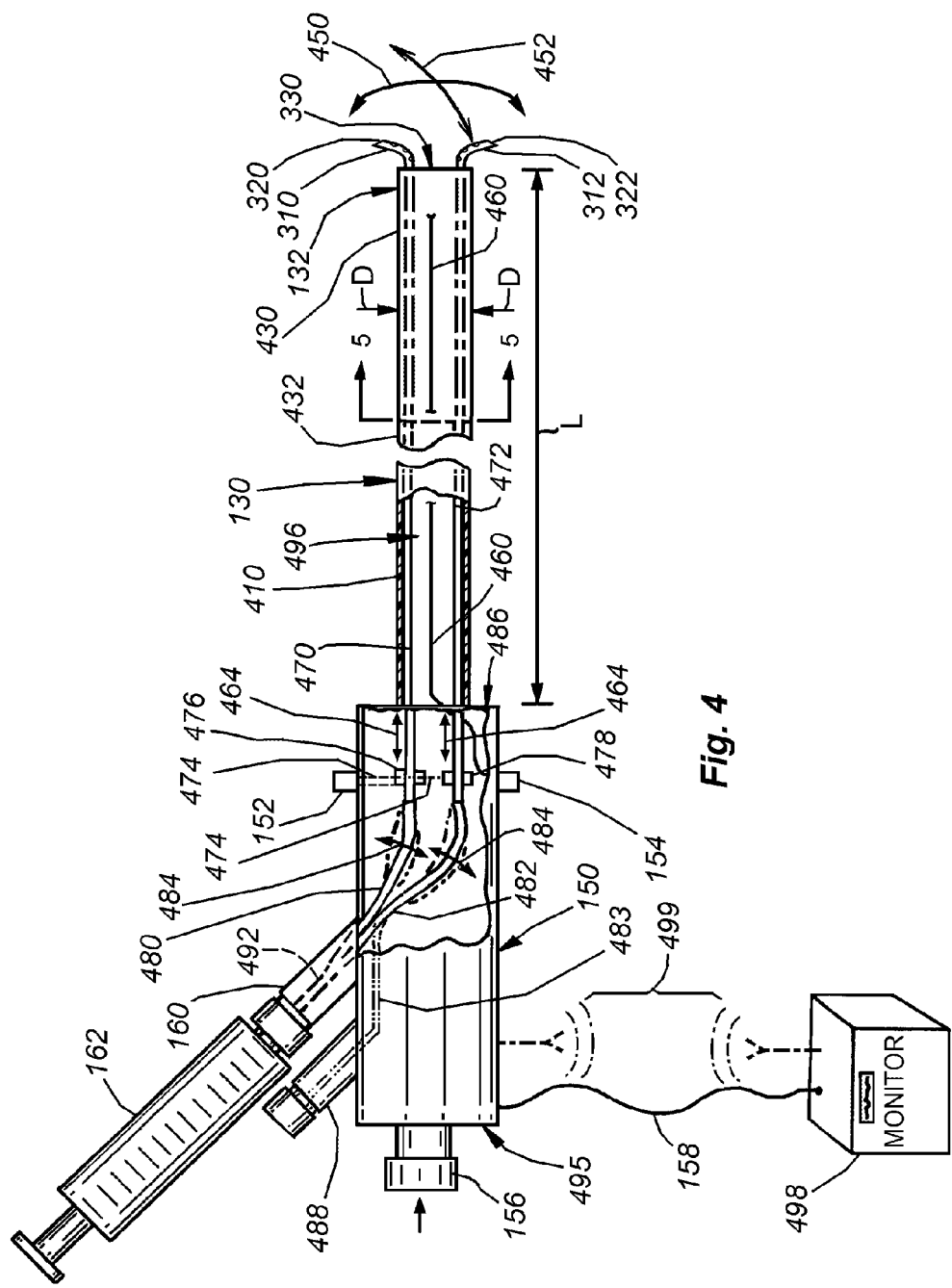
FIG. 4 is a partially exposed side view of the catheter and associated handle according to an illustrative embodiment of this invention with extensible needles extended from the distal end thereof.

Having described some basic considerations regarding the function and use of the catheter 130 according to an embodiment of this invention the structure of the catheter is now further described with reference to FIG. 4. The catheter 130 defines a hollow tubular catheter shaft 410 having a proximal end 420 and a distal end 132 with an opening at the tip 330. In an illustrative embodiment, the distal end 132 of the shaft 410 has at least two bendable regions, illustrated here as first bendable region 430 proximal to the distal end 132 of said shaft 410 and second bendable region 432 more proximal to distal end 132 of shaft 410. The two bendable regions allow bending in two orthogonal planes, depicted by orthogonal, curved arrows 450 and 452. The ability of the catheter shaft 410 to be controllably bent in two bending regions, provides for accurate position of the distal end 132 of the shat 410. The trigger assembly 154 generally enables the operator to bend the tip 330 by approximately 180° so as form a bend in the shaft 410 of the catheter 130 of approximately 90° in either direction. This provides for the needles 310, 312 to be positioned exactly for accurate injection. For DNA therapy this is significant so that only the desired cells will receive and express the therapeutic genes, and so that the genes will not be systematically distributed. A cable assembly 460, which can be of conventional design, acts as a linkage between the trigger assembly 154 and the distal end 132 of the shaft 410 to allow the one or more bending regions 430, 432 to bend in various axes (e.g. arrows 450, 452). The cable assembly 460 may be one or more cables that are operatively connected with portions of the inner wall of the shaft 410, and thereby exert tension under control of the trigger 154 to cause portions of the bending regions to flex in response to the applied tension.

Also illustrated on the handle 150 is a trigger assembly 152 for retracting and extending (arrows 464) the needles 310 and 312 from the tip 330. Note that it is expressly contemplated that the trigger mechanism 152 can be bifurcated to selectively extend each of the needles 310, 312 separately in alternate embodiments. The implementation of the linkage between the trigger assembly 152 and the elongated shafts 470 and 472 of the respective needles 310 and 312 can be any acceptable interconnection and is, this shown as a series of dashed lines 474 in FIG. 4. This linkage 474 engages anchor assemblies 476 and 478 on the proximal end of each needle shaft 470, 472 that serve to drive the shafts distally and proximally as needed. The proximal ends of the shafts include tubes 480, 482, 483 that communicate with one or more injection ports 160 and 488. The tubes 480, 482 and 483 allow flexure (shown in phantom and via arrows 484) to compensate for distal and proximal movement (arrows 464) of the needle shafts 470, 472.

The precise arrangement of injection ports on the handle 150 is highly variable. In this embodiment a pair of ports 160 and 488 is provided, each port being capable of accepting a different syringe (162 shown) containing a different agent. In such an arrangement, at least two discrete agents can be simultaneously delivered to needles 310 and 312. To accomplish this, the tube 483 is shown alternatively connected to the needle shaft 472. Thus, in one arrangement, the port 160 is adapted to deliver an agent to the shaft 470 and needle 310 and the port 488 is adapted to deliver an agent to the shaft 472 and needle 312. In an alternate arrangement, the one port 160 (for example) delivers an agent to both shafts and needles via (for example) a Y-connection 492. Appropriate fluid gates and valves (not shown) can be employed to control which port delivers and agent to a given needle. In addition, in alternate embodiments, it is contemplated that the handle may, itself store supplies of agent onboard. By way of example a handle with a variety of desirable steering, dose-metering, dose-indicating and trigger functions is taught by the "SteeraJet™" percutaneous catheter injection system available from Micro-Heart of Sunnyvale, Calif.

Note also that the trigger assembly 152 may be spring-loaded and/or include various locking mechanism and safety catches (not shown) to prevent unintended extension on a needle and/or lock an extended needle in place as desired. While also not shown the handle can include a locking base between the shaft 410 and handle's distal end 486. Such a base would include various connectors to enable the functional parts (electronic, fluid-transmitting and mechanical) to be attached to of the shaft 410 of the catheter to be quickly attached to and released from the handle.

The handle's proximal end 495 includes a proximal hub 156 that allows injection of an agent (fluid or gas) to the tip via the shaft's main lumen 496. The hub can comprise an electrical connector for various functions in certain embodiments. Alternatively, the proximal hub 156 allows insertion of a smaller catheter (not shown) that is guided via the shaft's lumen 494 to the tip 330. Such a smaller catheter can include one or more probes, sensors or mechanisms on its distal end. Alternatively, such a smaller catheter can include another fluid-delivery tip.

As discussed further below the tip of the needles 310, 312 and/or shaft tip 330 can include solid state, electronic sensors that are operatively connected to the handle. The handle includes an electrical connection (or connections) 158 that transfers signals from one or more sensors to a monitor 498 of appropriate type. In an alternate embodiment, the connection can be made via a wireless implementation 499 employing (for example) radio-frequency communication/data transfer operating in accordance with IEEE Standard 802.11 (a, b, g, etc.).

The length L of the catheter shaft 410 is highly variable, and depends, in part, on the chosen path for insertion into the body and target organ. In one embodiment, the length L is between approximately 60 centimeters and 80 centimeters, but other lengths are expressly contemplated. The approximate diameter D of the shaft, in one embodiment is a standard 6-7 French.

Figure 5A:
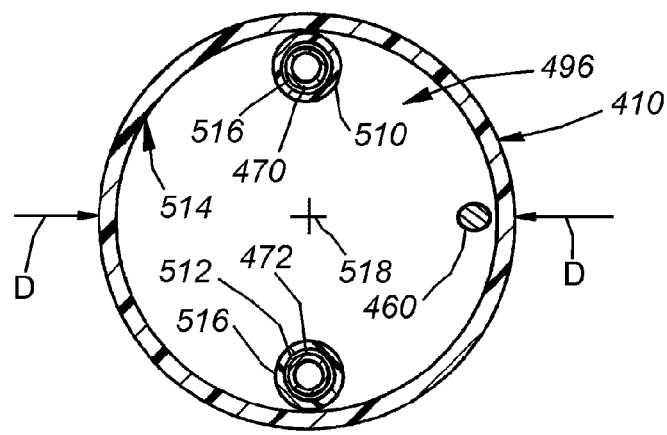
FIG. 5A is a side cross section of a first embodiment of the catheter taken along line 5-5 of FIG. 4.
Figure 5B:
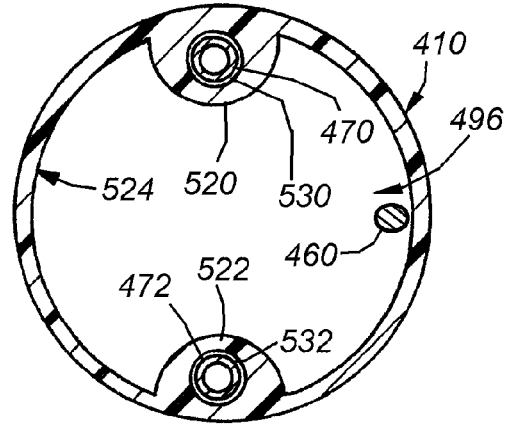
FIG. 5B is a side cross section of a second embodiment of the catheter taken along line 5-5 of FIG. 4.
Figure 5C:
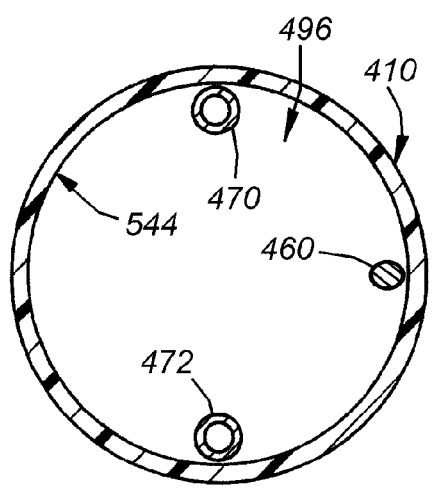
FIG. 5C is a side cross section of a third embodiment of the catheter taken along line 5-5 of FIG. 4.

Reference is now made to the catheter shaft (410) cross sections of FIGS. 5A, 5B and 5C, which depict three possible alternate embodiments for transmitting the needle shafts 470, 472 along the inner wall of the main lumen 496. In a first embodiment (FIG. 5A), the needle the shafts 470 and 472 are contained within closely-conforming sheaths 510 and 512, respectively that confront the inner wall 514 of the main lumen 496, and are adhered to the inner wall 514 at a contact line 516 therebetween. The sheaths 510, 512 extend parallel to the central axis 518 of the main lumen 496 on opposite sides of the axis 518. Adhesion of the sheaths 510, 512 to the inner wall 514 can be accomplished by thermal or ultrasonic welding, adhesives, molding or extruding the shaft 410 and sheaths 510, 512 together or by any other acceptable technique. Alternatively, the sheaths 510, 512 may remain unadhered to the inner wall 514, and simply lay against it. The shaft material (NiTiNOL in an illustrative embodiment), has sufficient rigidity to resist bucking or binding, and thus it may be maintained in an unadhered sheath in certain embodiments.

In another embodiment of the catheter shaft (410) cross section (FIG. 5B), the shaft inner wall 524 includes a pair of opposing inner-facing protrusions 520 and 522 that define needle-shaft lumens 530, 532 extending axially along the shaft 410. These protrusions 520, 522 are typically molded or extruded into the inner wall 524 at the time of shaft construction. However alternate construction techniques, such as welding a lumen-containing component to the inner wall is also contemplated.

Alternatively, the needle shafts 470, 472 may be simply passed through the main lumen 496 of the shaft 410 with no surrounding sheath as shown in the embodiment of FIG. 5C. This arrangement relies upon the rigidity/elasticity of the shaft material to ensure no bucking or binding occurs. In such an embodiment, it is contemplated that the distal tip 330 of the shaft will typically contain a guide (see below) that restrains the needles 310, 312 so that they are properly guided out of the tip during extension.

Figure 6:
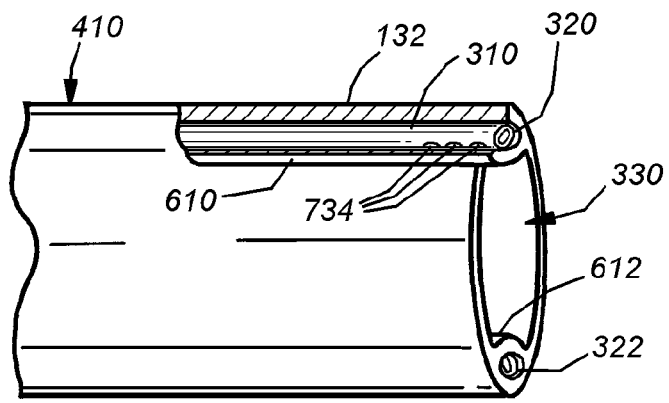
FIGS. 6 and 6A are fragmentary perspective views of the distal end of the catheter of FIG. 4 detailing the extensible needles in a retracted and extended orientation, respectively.
Figure 6A:
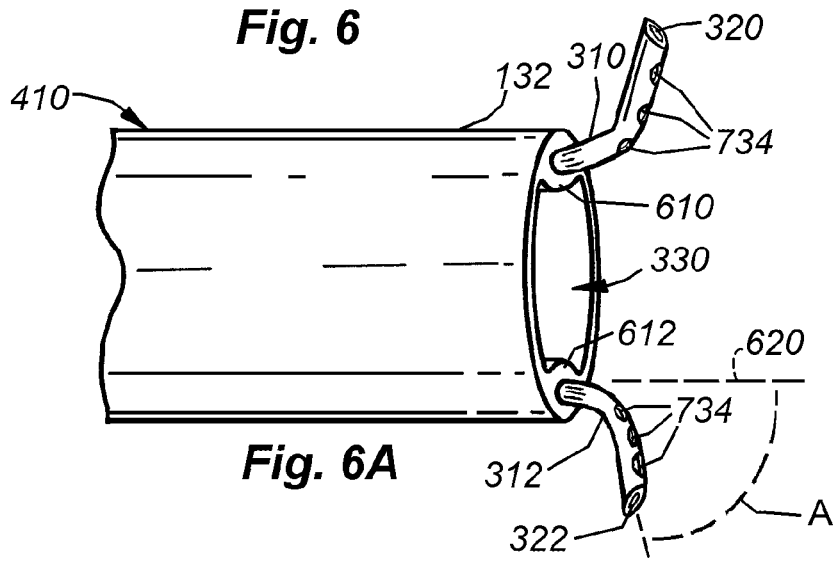

As shown in FIGS. 6 and 6A, the needles 310, 312 are respectively retracted and extended from the tip 330 of the catheter shaft 410. When retracted (FIG. 6), the surrounding sheath 610, 612 restricts flexure of the needles and maintains them in a highly linear orientation (e.g. straight). The tips 320, 322 are unexposed, thereby reducing or preventing the risk of an inadvertent puncture or abrasion on non-target areas. When extended as shown in FIG. 6A through activation of the handle's trigger mechanism (152), the needles 310, 312 exhibit the illustrated contralateral projection. When so projecting, their approximate length is between about 4 and 7 millimeters in an illustrative (myocardium-engaging) embodiment, but other projection lengths are expressly contemplated. The approximate angle of projection A relative to the shaft's axial direction (dashed line 620) is between approximately 70 and 80 degrees in this embodiment. In alternate embodiments, a greater or lesser angle can be employed.

The choice of projection angle and projection length is chosen, in part, upon the nature of the tissue into which the needles are intended to project and the material performance of the needles themselves. Where a tissue surface is relatively thin, a high angle and short length of projection are desired. However, the angle should not be 90 degrees or greater at the juncture of the tip because this would prevent desired penetration of the needles into the adjacent tissue upon extension—in other words, the needles may simply glance the surface of the organ. As shown generally in FIG. 7 a needle shape that includes an initial, distal segment 714 that (when fully extended) causes the needles to be directed contralaterally, followed by a proximal segment 716 that ensures some depth of penetration is typically desirable.

Because the needles extend at a controlled angle in contralateral directions, the depth can be fixed at a given maximum (i.e. depth/extension adjustment is typically unnecessary) with relative assurance that the organ wall is not being punctured. Rather, the needles extend within and along the inner thickness of the wall for maximum exposure of agents to areas of treatment. This is particularly significant for treating a thin postinfarction region, the right ventricle, or the septum. Patients having smaller and thinner cardiac walls generally represent a high risk and need a special approach for the injection catheter treatment. Other catheters are not recommended for use in myocardial regions estimated to be less than 6 mm thick due to the potential for cardiac perforation or ventricular tears. Using the catheter of the present invention under such circumstances, however, presents no such contraindication.

In an exemplary embodiment, the needles 310, 312 have a size of a standard, slim 28-26 G. Other sizes and shapes are expressly contemplated. The needle tips 320 and 322 have a characteristic chisel shape in this embodiment that ends in a tip aperture 730 (FIG. 7) for delivering agent (arrow 724) therefrom. Furthermore, the needles 310, 312 of this embodiment also include body apertures 734 that allow for further agent distribution (arrows 736) to adjacent tissue. The number and size of body apertures 734 is highly variable. In one embodiment 3-5 body apertures are provided, each being approximately 0.1 to 0.2 mm in diameter. The body apertures 734 are shown along the medial side of the needles 310, 312, but can be placed at other locations around the needle shaft in alternate embodiments. The presence of the multiple apertures of the penetrable elements ensures a rapid dispensation of the agents of choice, as well as for even infiltration of the agent in the tissue over a large area per injection providing more points of contact between the therapeutic and targeted tissue, such as myocardial tissue. The needles 310, 312 may be designed using the principle of the present invention so that the therapeutic agent may be administered, for example, as 250 micro-liters at four different sites within the myocardium, or, for example, as a 100 micro-liter injection at ten different sites in the myocardium. The plurality of apertures may be arranged in a staggered or random manner about the penetrable element providing for the minimization of back pressure upon injection of the therapeutic agent where such control is required.

Figure 7:
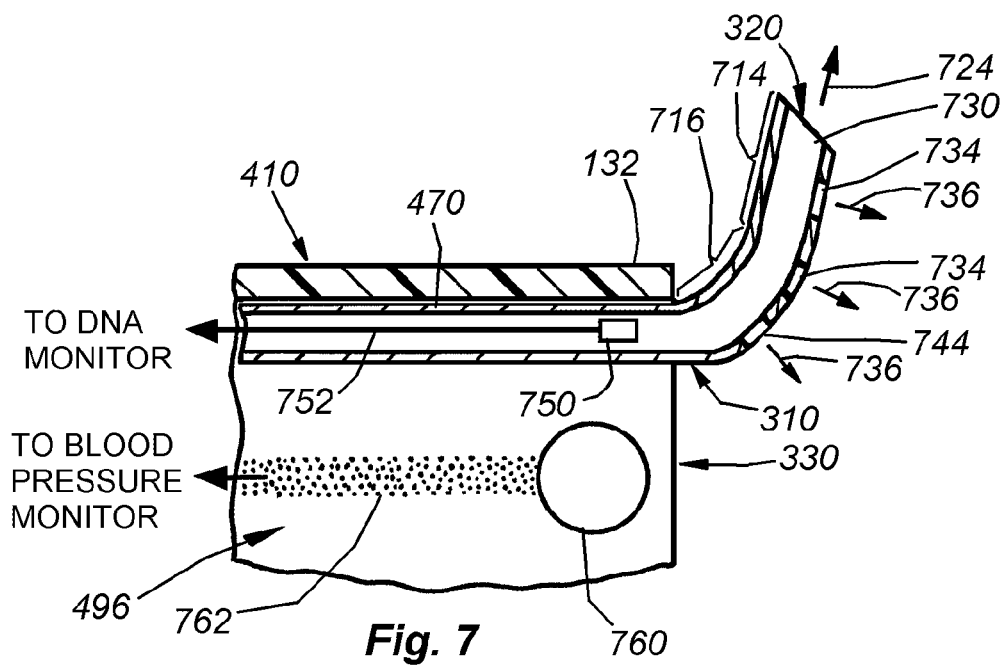
FIG. 7 is a partial side cross section of the distal end of the catheter of FIG. 4 detailing additional blood pressure and DNA-sensing devices according to an embodiment of this invention.

Referring further to FIG. 7, one or both needles 310, 312 can be provided with an appropriate sensor or monitor. In this example, the needle 310 has an internally provided DNA sensor 750 that determines when genetic material or other DNA-containing substances are traveling past the needle 310. This sensor can be connected by an electrical path (arrow 752) that is established using an appropriate conduit or by simply using the conductive properties of the shaft 470. Such a sensor can be interconnected with a monitor via the handle to inform the practitioner when a supply of genetic agent has been fully delivered (i.e. when there is no more indication of DNA in the stream).

Likewise, the shaft's main lumen 496 can be provided with a blood pressure sensor 760, or another device, such as a tissue-proximity sensor that determines when contact has been made with an organ. Signals from this sensor can be transmitted down the shaft using a conductive material 762, such as metal or graphite powder doped into the shaft wall.

Note that the materials used to construct the catheter shaft 410 and various internal sheaths can be widely varied. In general they should be non-allegenic and biocompatible, and should avoid flaking or release of materials in to the body. A variety of plastics including certain polyethylenes are suitable for this task. Appropriate non-stick coatings such as PTFE may be applied to exterior and interior surfaces of catheter components where appropriate.

The above-described catheter exhibits a number of clear advantages over prior art implementations. Unlike other catheters, the catheter of the present invention does not need any assisting monitoring, preliminary electromechanical left ventricular mapping, guidewire, guide-in-guide steerable delivery system, nor pressurized heparinized saline flush to operate the device.

Studies have shown that intramyocardially administered adenoviral vector itself causes only mild inflammation but no effusion, and only the higher doses of AdVEGFs cause extravasation of plasma to the pericardium so that a combined therapy might have the priority versus a single therapy, a situation well suited to the catheter of the present invention.

The small outer diameter of the shaft of the catheter will not contraindicate its use in patients with severe aortic valve stenosis. Moreover, it will allow use of other than the femoral access site, such as the radial artery on the arm in case the patient is diagnosed with Leriche syndrome or other atherosclerotic impairments or cannot be restricted in moving since after the puncture in groin the patient would be obliged to stay in bed for a certain period of time.

The design of the catheter provides for contrast media to be injected through its central lumen to enable coronaro- or ventriculography, thus, accelerating the overall procedure. The needles are impregnated with a special material (parylene, polyimide, or teflon coating) in order to avoid inactivation of adenovirus vector infectivity, hence the device provides for more catheter/vector compatibility. The innovative technology/design of the catheter, as described, improves clinical, economic, and patient satisfaction outcomes.

The simple design of the catheter makes its use easy and easy to learn avoiding special long training courses, having expensive assisting devices, or the need for an assistant. A syringe attaching site is designed in a way that it makes it equally useful for both right- and left-handed operators.

The forgoing has been a detailed description of certain illustrative embodiments of the invention. Various modifications and additions can be made without departing from the spirit and scope of this invention. For example, a variety of handle designs and interconnections with the catheter shaft can be implemented according to alternate embodiments. The number of lumens and the size and arrangement of these lumens can also be varied. The number of needles and the manner of extension and retraction can be varied as well. In one alternate embodiment each of the two needles can be deployed separately, by a separate trigger action. In another embodiment, only one curved needle of the general function, form and shape described herein may be employed. Further, in another embodiment, three or more curved needles of a general function, form and shape described herein can be employed at the catheter tip, all being operated simultaneously or separately in various alternate embodiments. Also, while body apertures are shown on both needles, in an alternate embodiment only one of the needles may contain body apertures. Alternatively, the size, number and/or locations of apertures for each needle may vary depending upon the type and amount of agent to be delivered from each needle. Accordingly, this description is meant to be taken only by way of example and dot to otherwise limit the scope of this invention.

What is claimed is:

1. A method for delivering agents to an interior of a right ventricle of a heart comprising:
   inserting a catheter having a shaft into a subclavial vein and steering the shaft into the right ventricle;
   moving a distal tip of the catheter into contact with a predetermined area of the right ventricle;
   extending a first injection needle and a second injection needle from the distal tip in contralateral directions to engage tissue of the organ and anchor within the tissue; and
   delivering through the injection needles a predetermined agent to the tissue;
   wherein the step of delivering includes directing the agent through a plurality of body apertures that are spacedly disposed along a medial side of each of said first and second injection needles so as to deliver the agent in a direction facing away from the distal tip of the catheter;
   wherein the step of extending the needles includes providing a nested position thereof and providing a deployed position thereof;
   wherein, in the deployed position, the contralateral direction to engage tissue places the respective needle tips facing away from each other while the plurality of body apertures on the medial side are directed away from the catheter shaft;
   wherein, for the deployed position, the needles assume a curvilinear/bent shape that, when extended, exhibits a nearly perpendicular direction of extension in each of opposing directions of extension.

2. The method as set forth in claim 1 wherein the step of delivering includes providing a separate agent to each of the first injection needle and the second injection needle deploying includes deploying the respective needles in opposed diametric directions from diametric position at the tip of the catheter shaft.

3. The method as set forth in claim 1 wherein the step of delivering also includes directing the agent through a distal tip aperture.

4. The method as set forth in claim 1 wherein the step of moving the distal tip of the catheter includes remotely controllably bending at least one bend region disposed along the catheter shaft.

5. The method as set forth in claim 4 including a first bendable region proximal to the distal tip of the catheter shaft and a second bendable region separate from the first bendable region and more proximal to distal tip of the catheter shaft.

6. The method as set forth in claim 5 wherein the two bendable regions allow bending in two orthogonal planes.

7. The method as set forth in claim 5 including a proximal control member manipulated to control bending from a location remote from said catheter tip.

8. The method as set forth in claim 1 wherein the main lumen distal end is defined by a distal end flat contact surface that engages the tissue as the first and second injection needles are anchored into the tissue to a depth that eliminates the possibility of myocardial perforation.

9. A method for delivering agents to an interior of a right ventricle of a heart comprising:
   inserting a catheter having a shaft into a subclavial vein and steering the shaft into the right ventricle;
   moving a distal tip of the catheter into contact with a predetermined area of the right ventricle;
   extending a first injection needle and a second injection needle from the distal tip in contralateral directions to engage tissue of the organ and anchor within the tissue; and
   delivering through the injection needles a predetermined agent to the tissue;
   wherein the step of moving the distal tip of the catheter includes remotely controllably bending at least one bend region disposed along the catheter shaft;
   the bend region including a first bendable region proximal to the distal tip of the catheter shaft and a second bendable region separate from the first bendable region and more proximal to distal tip of the catheter shaft;
   wherein the two bendable regions allow bending in two orthogonal planes;
   and controlling the respective bend regions from a proximal control member that is mounted at a proximal end of the catheter shaft.

10. The method as set forth in claim 9 wherein the step of delivering includes directing the agent through a plurality of body apertures that are spacedly disposed along a medial side of at least one of said first and second injection needles.

11. The method as set forth in claim 10 wherein the step of delivering includes directing the agent through a plurality of body apertures that are spacedly disposed along a medial side of both of said first and second injection needles the step of extending the needles includes providing a nested position thereof and providing a deployed position thereof; wherein, in the deployed position, the contralateral direction to engage tissue places the respective needle tips facing away from each other while the plurality of body apertures on the medial side are directed away from the catheter shaft; and wherein, for the deployed position, the needles assume a curvilinear/bent shape that, when extended, exhibits a nearly perpendicular direction of extension in each of opposing directions of extension.

12. The method as set forth in claim 9 including a first bendable region proximal to the distal tip of the catheter shaft and a second bendable region separate from the first bendable region and more proximal to distal tip of the catheter shaft 22 wherein the step of deploying includes deploying the respective needles in opposed diametric directions from diametric position at the tip of the catheter.

13. The method as set forth in claim 12 wherein the two bendable regions allow bending in two orthogonal planes 20 including respective cabling coupled from the proximal control member for controlling respective bend regions.

14. The method as set forth in claim 9 including a proximal control member manipulated to control bending from a location remote from said catheter tip.

15. The method as set forth in claim 9 wherein the main lumen distal end is defined by a distal end flat contact surface that engages the tissue as the first and second injection needles are anchored into the tissue to a depth that eliminates the possibility of myocardial perforation.

16. A method for delivering agents to an interior of a right ventricle of a heart comprising:

inserting a catheter having a shaft into a subclavial vein and steering the shaft into the right ventricle;

moving a distal tip of the catheter into contact with a predetermined area of the right ventricle;

extending a first injection needle and a second injection needle from the distal tip in contralateral directions to engage tissue of the organ and anchor within the tissue; and delivering through the injection needles a predetermined agent to the tissue; controlling the first needle and the second needle separately for axial movement controlled from a trigger member so as to separately and respectively drive the first needle and the second needle in each of a refracted position and an extended position.

17. The method as set forth in claim 16 wherein the injection needles have and an extended position in which the first needle and the second needle extend distally contralaterally from the first needle distal end and the second needle distal end, respectively, in each of opposing directions to thereby define, along at least a portion therealong, a nearly perpendicular direction of extension with respect to an axis of the shaft tip and thereby anchoring each of the first needle and the second needle into tissue with the shaft tip confronting the tissue.

18. The method as set forth in claim 17 wherein the trigger member comprises first and second control members for separately and selectively controlling the drive of the respective first and second needles.

19. The method as set forth in claim 16 wherein the step of moving the distal tip of the catheter includes remotely controllably bending at least one bend region disposed along the catheter shaft.

20. The method as set forth in claim 19 including providing a trigger assembly at its proximal end that includes first and second trigger members, said first trigger member controlling the bendable movement of the distal end of the catheter shaft at a first bendable region, thereby allowing the shaft tip to bend so as to be steerable for positioning of the distal end of the catheter shaft.

21. The method as set forth in claim 20 including a second trigger member for controlling banding at a second bendable region spaced from said first bendable region.

22. The method as set forth in claim 17 wherein the step of delivering includes directing the agent through a plurality of body apertures that are spacedly disposed along a medial side of at least one of said first and second injection needles.

* * * * *